United States Patent
Bob et al.

(10) Patent No.: US 7,311,659 B2
(45) Date of Patent: Dec. 25, 2007

(54) ENDOSCOPE SHAFT

(75) Inventors: Konstantin Bob, Weinheim (DE); Wolfgang Kast, Dirdorf (DE)

(73) Assignee: STM Medizintechnik Stamberg GmbH, Weinheim (DE)

( * ) Notice: Subject to any disclaimer, the term of this patent is extended or adjusted under 35 U.S.C. 154(b) by 151 days.

(21) Appl. No.: 10/832,523

(22) Filed: Apr. 27, 2004

(65) Prior Publication Data

US 2005/0004434 A1   Jan. 6, 2005

(30) Foreign Application Priority Data

May 5, 2003   (DE)   ............................. 103 20 228

(51) Int. Cl.
*A61B 1/00*   (2006.01)
*A61B 1/12*   (2006.01)

(52) U.S. Cl. ............... 600/153; 600/139; 600/156

(58) Field of Classification Search ............ 600/205, 600/209, 121–125, 153–159
See application file for complete search history.

(56) References Cited

U.S. PATENT DOCUMENTS

| 4,589,404 | A | * | 5/1986 | Barath et al. ............... 600/108 |
| 4,753,223 | A | * | 6/1988 | Bremer ....................... 600/140 |
| 4,805,595 | A | | 2/1989 | Kanbara |
| 4,878,492 | A | * | 11/1989 | Sinofsky et al. ............... 606/7 |
| 4,900,314 | A | | 2/1990 | Keine |
| 4,928,699 | A | | 5/1990 | Sasai |
| 5,201,908 | A | * | 4/1993 | Jones ......................... 600/123 |
| 5,575,753 | A | * | 11/1996 | Yabe et al. ................. 600/123 |
| 5,643,175 | A | * | 7/1997 | Adair .......................... 600/133 |
| 6,249,708 | B1 | * | 6/2001 | Nelson et al. ............. 607/122 |
| 2004/0236306 | A1 | * | 11/2004 | Lin et al. ................... 604/500 |

FOREIGN PATENT DOCUMENTS

| DE | 3712643 | 8/1988 |
| DE | 4413026 | 10/1995 |
| JP | 07184828 | 7/1995 |
| WO | 9951283 | 10/1999 |

* cited by examiner

*Primary Examiner*—John P. Leubecker
*Assistant Examiner*—Philip R Smith
(74) *Attorney, Agent, or Firm*—Hanley, Flight, & Zimmerman, LLC

(57) ABSTRACT

An endoscope shaft comprising a working conduit and a number of supply and/or functional conduits. The supply and/or functional conduits have an excessive length with respect to the endoscope shaft and are arranged in spirals, in serpentine and/or zigzag shape around or along the working conduit, whereby a flexibility and bendability of the endoscope shaft is achieved.

9 Claims, 6 Drawing Sheets

ENDOSCOPE SHAFT

BACKGROUND OF THE INVENTION

The present invention relates to an endoscope shaft.

Endoscopes are instruments especially for exploring cavities or tube-shaped canals of the body, for instance for medical purposes. Endoscopes of this kind are preferably used for exploring the gullet, the stomach, the duodenum from the stomach, the intestine from the anus, the urethra, the vesica and the ureter. Endoscopes are mostly equipped with a lighting device at their front end and with an optical system for visually detecting the area of the body cavity or body canal located forward thereof.

Further, endoscopes usually comprise a working conduit, as it is called, through which various working instruments can be introduced and operated, e.g. forceps for taking tissue samples, biopsy needles, heatable cutting wires, small scissors or the like. Finally, as a rule, functional conduits, for instance a fluid conduit for wash and operating wires for bending the front end of the endoscope in various directions, are provided. Altogether the endoscope has, apart from its rear operating end and a connecting cord, an elongated flexible bar and/or shaft shape. The common outer diameters approximately range from 9 to 15 mm and are slightly larger at the front head.

So far, endoscopes have been introduced into the body by the physician pushing the pressure-stiff endoscope and/or the pressure-stiff endoscope shaft into the body from the part of the endoscope protruding from the body. This way of introducing the endoscope is particulary laborious, difficult and also extremely painful for the patient, especially in the case of the coloscope, as in the latter case the intestine has bends and frequently isthmuses which the endoscope shaft has to follow. Accordingly, coloscopic examinations so far have been complex examinations which are unpleasant and painful for the patient. Moreover the handling of a coloscope requires a physician experienced in this matter.

Furthermore, prior art has shown that endoscopes of the know construction represent extremely complicated and thus cost-intensive designs due to the stiffness required for inserting them into the patient's cavity to be examined, while at the same time they have to be flexible. These constructions are so expensive that they have to be employed again and again. Therefore, it is necessary to take complex cleaning and sanitary measures after each examination, which also bears a risk of damaging the endoscope shaft in the end, especially when such cleaning operations are carried out by untrained staff. Moreover the bending radii to be achieved are so large that an examination substantially without pain of an intestine wall, for instance, is not possible.

In view of this situation, it is an object of the invention to provide an endoscope shaft having better characteristics for example with respect to its flexibility.

SUMMARY OF THE INVENTION

The foregoing object of the invention is achieved by an endoscope shaft having a working conduit and a number of supply and/or functional conduits with the supply and/or functional conduits having excessive length with respect to the endoscope shaft.

Accordingly, the core of the invention substantially consists in designing the endoscope shaft to have a working conduit and a number of supply and/or functional conduits which are arranged in the endoscope shaft such that they are adapted to extend in the longitudinal direction of the shaft by virtue of their arrangement.

In principle, this is achieved by the fact that the conduits have an excessive length with respect to the endoscope shaft. In this way, the bending behavior is less impaired by the supply and/or functional conduits. Moreover, the endoscope shaft can now be bent without giving rise to the risk that the conduit walls start to tear.

In an advantageous manner, the supply and/or functional conduit(s) which is/are usually located eccentrically in the endoscope shaft is/are arranged according to the invention to extend spirally around the working conduit or in serpentine or zigzag shape in the longitudinal direction of the endoscope shaft or in a combination of these measures. In this way, the flexibility of the endoscope shaft is less dependent on the characteristics of the materials used for the conduits, but the flexibility is obtained by the shaping and arrangement of the conduits as a helix according to the invention. By this design, bending diameters of less than 30 mm can be achieved without a break-up of the conduit walls occurring.

It is especially advantageous to connect the supply and/or functional conduits as well as preferably also the cables or fibers in advance to form a flat strip which is wound spirally and whose one flat side at the same time forms the inner wall of the working conduit. In this context, it is emphasized, however, that instead of the flat strip there are also other possibilities of design, of course, such as a conduit hose package and the like.

The supply conduits and/or functional conduits need not necessarily have a round profile as is described, inter alia, in some of the following embodiments, but they may have any shape suited for permitting a more compact construction. So the conduits may for instance have a rectangular or triangular shape or may be formed directly by the flat strip material, for instance by extrusion molding.

It has also turned out to be advantageous to manufacture the endoscope shaft of synthetic resin foam in which the supply and functional conduits are embedded or formed. Such foam material forms on its surface, i.e. the surface shell of the endoscope shaft, pores, indentations and similar surface depression which, when bending the endoscope shaft, cause a bellows effect, that is they reduce the surface tension due to pulling apart or folding up surface folds.

Further advantageous configurations of the invention are the subject matter of the claims.

BRIEF DESCRIPTION OF THE DRAWINGS

Hereinafter, the invention will be described in detail by way of preferred embodiments with reference to the accompanying drawings, in which.

DETAILED DESCRIPTION OF THE PREFERRED EMBODIMENTS

Figure 1:
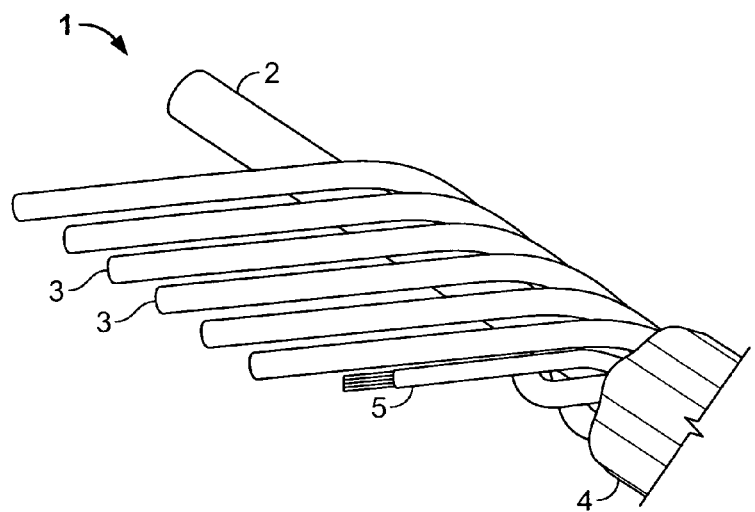
FIG. 1 shows a partially broken functional view of an endoscope shaft comprising a working conduit and spirally arranged individual supply and/or functional conduits according to a first preferred embodiment of the invention.

As one can take especially from FIG. 1, an endoscope shaft 1 according to the first preferred embodiment of the invention includes or forms a working conduit 2 and a number of supply and/or functional conduits 3. The supply and/or functional conduits 3 are spirally wound and extend around the substantially central working conduit 2.

As a rule, the endoscope shaft 1 designed in this way includes at its distal end an endoscope head (not shown in detail) which is connected through the supply conduits 3 to an operating means, likewise not illustrated, which is preferably arranged at the proximal end of the endoscope shaft 1. The endoscope head includes a number of use-specific functional members such as an optical means, lighting means, spraying nozzles, movable lenses and/or mirrors and the like which are operable through the supply conduits 3 by the operating means. Moreover, the distal end portion of the endoscope shaft 1 is preferably designed as a bendable joint member that is connected to the functional conduits 3 and likewise e.g. hydraulically adjustable and/or movable by the operating means.

It is pointed out in this context that the design of such bendable end pieces for endoscope shafts as well as the structure of endoscope heads already belong to the prior art and have been published also by the inventor of the present shaft design itself in a plurality of patent applications. In so far, a detailed description of the endoscope head and of the bendable end piece can be dispensed with in this context.

Figure 1A:
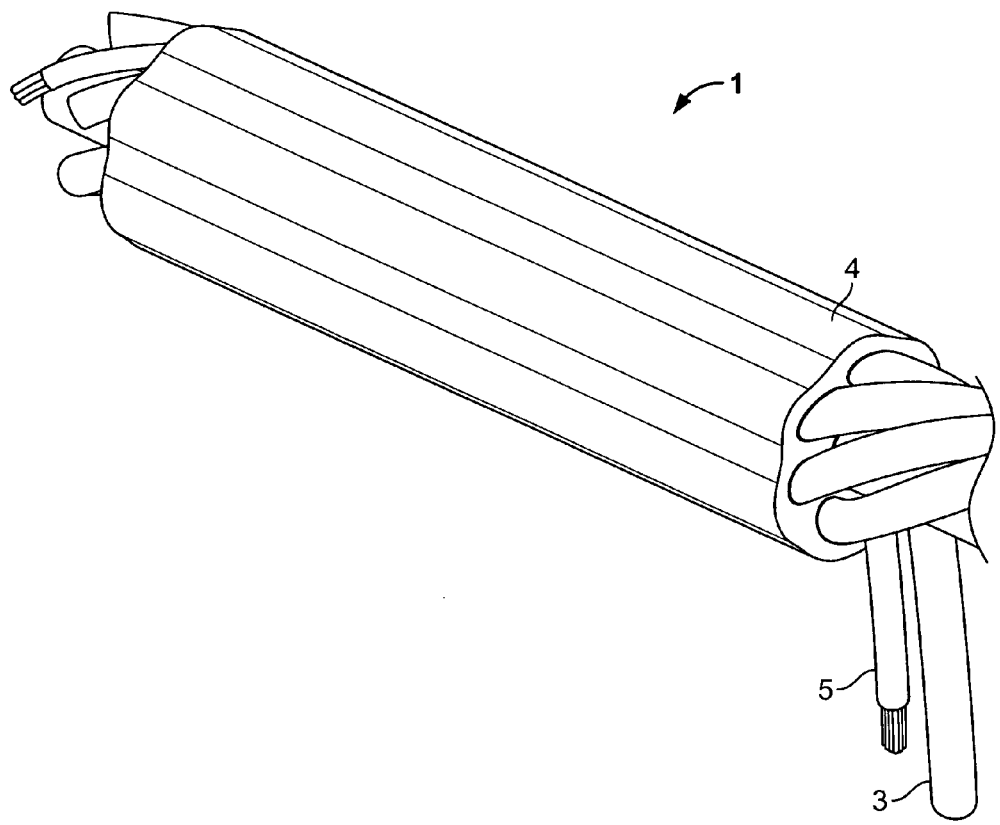
FIG. 1a is a perspective view of the endoscope shaft according to FIG. 1.

According to FIG. 1, the working conduit 2 is formed in this first embodiment by a flexible tube or hose, preferably of a plastic material, around which an envelope 4 preferably of synthetic resin foam is shaped. As one can take from FIG. 1a, in this envelope 4 the supply and/or functional conduits 3 are embedded and are wound individually at a predetermined parallel distance from each other as well as preferably in an angular symmetry around the working conduit 2 to form a spiral having a defined gradient. There is moreover provided a fiber or cable bundle 5 which is spirally guided in parallel to the supply and/or functional conduits 3 likewise around the working conduit 2 and is embedded in the envelope 4. The supply and/or functional conduits 3 and the cable bundle 5 are arranged at a predetermined radial distance from the working conduit 2, however, so that they are completely enclosed by the envelope material. This guarantees that the inner wall of the working conduit 2 is not indented by the circumferential conduits 3 or cables 5 even when the endoscope shaft 1 is maximally bent. In the present case, the supply and/or functional conduits 3 consist of a tubular section of plastic material having a predetermined flexibility so that the spirally arranged supply and/or functional conduits 3 can be pulled apart without high resistance, so that the conduit walls do not break or start to tear.

An alternative configuration to the afore-described first embodiment consists in the fact that the working conduit 2 is not provided as a separate component but is designed when shaping the envelope 4. In other words, the tubular working conduit 2 can be replaced by a mandrel around which the supply and/or functional conduits 3 as well as preferably the fiber or cable bundle 5 are wound. Subsequently, the envelope 4 is formed around the mandrel for instance by foaming, extruding or casting, wherein a smooth inner wall is formed on the surface of the mandrel. Finally, the mandrel is withdrawn from the hardened envelope material whereby the working conduit 2 is formed by the envelope material itself. The supply and/or functional conduits 3 may be manufactured in a corresponding manner, i.e. may be formed by the envelope material itself.

Figure 2:
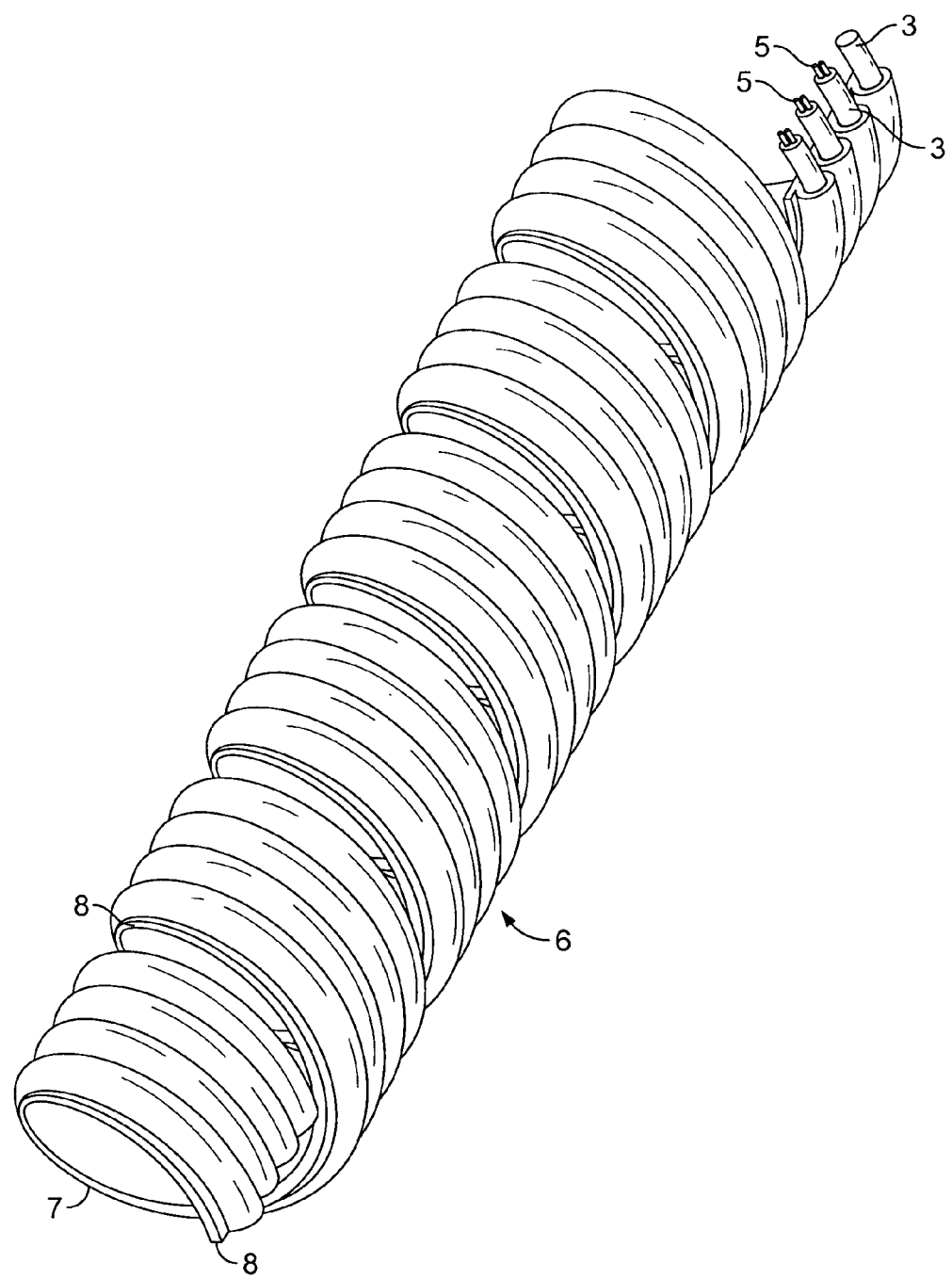
FIG. 2 shows a functional view of spirally arranged supply and/or functional conduits according to a second preferred embodiment of the invention which are combined to and/or integrated in a flat strip.
Figure 3:
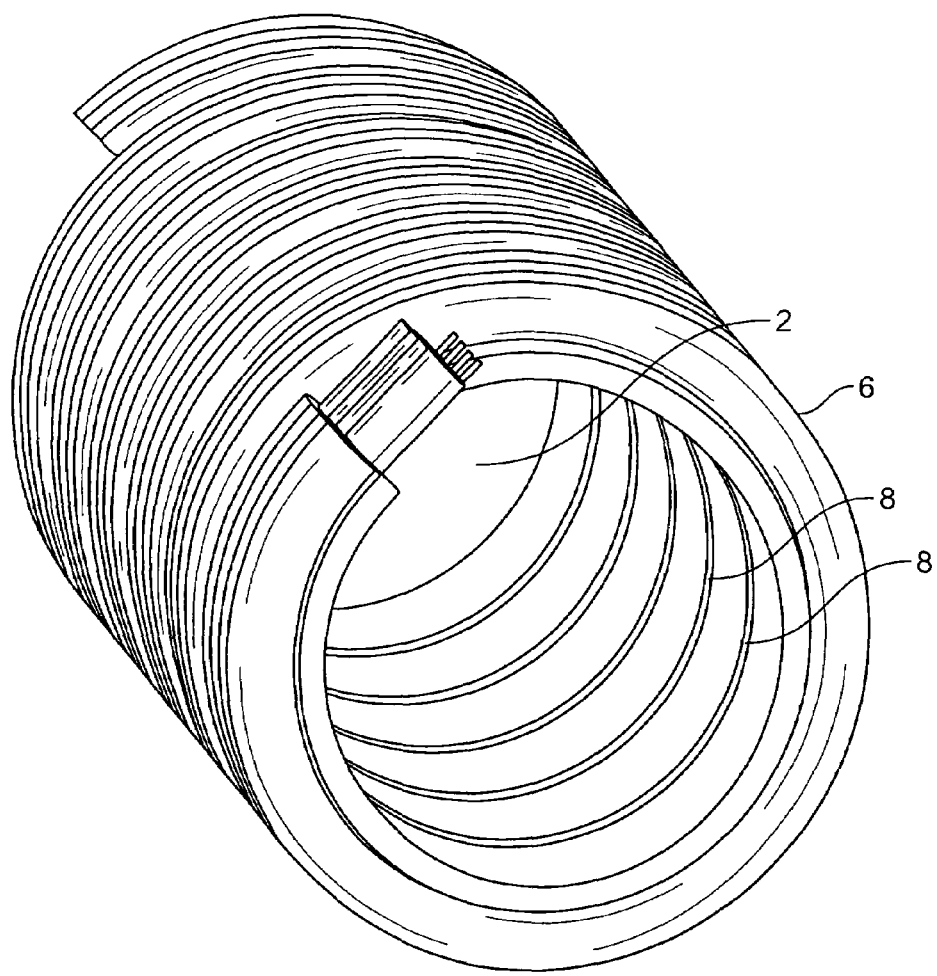
FIG. 3 is a perspective view of a part of the endoscope shaft formed by a flat strip according to the second preferred embodiment of the invention.

In FIGS. 2 and 3, a second preferred embodiment of the invention is shown. In this case, the supply and/or functional conduits 3 as well as preferably also the cables and/or fibers 5 are combined into a flat strip 6. That is to say, the conduits 3 and possibly the cables and fibers 5 are enclosed by a plastic material which is shaped into a strip-like flat cord having a substantially smooth side face 7. This flat strip 6 is subsequently shaped into a spiral in such a way that no inherent torsion of the strip 6 occurs, i.e. the at least one smooth side face 7 always forms the inside of the spiral.

As one can take especially from FIG. 2, the conduits 3 are manufactured of tubes preferably of a plastic material which are then enclosed by a further synthetic envelope, preferably synthetic resin foam, which is shaped into the flat strip section and connects the tubes to form a unit. In the second embodiment, the cables or fibers 5 are arranged individually or in thin fiber bundles (including few fibers) between the tubes in the envelope material. This separation of the fibers/cables 5 increases the flexibility of the flat strip 6 and simultaneously improves the homogeneity of the same.

The flat strip spiral preformed in this way is subsequently glued or welded at the respective longitudinal edges 8, thus forming the radially closed working conduit 2, as this is shown in FIG. 3 The longitudinal edges 8 may be either butt-welded/glued or may slightly overlap, to which purpose in the latter case the flat strip edges 8 are thinned in the overlapping area so as to avoid material enlargements at the finished endoscope shaft 1.

Figure 4:
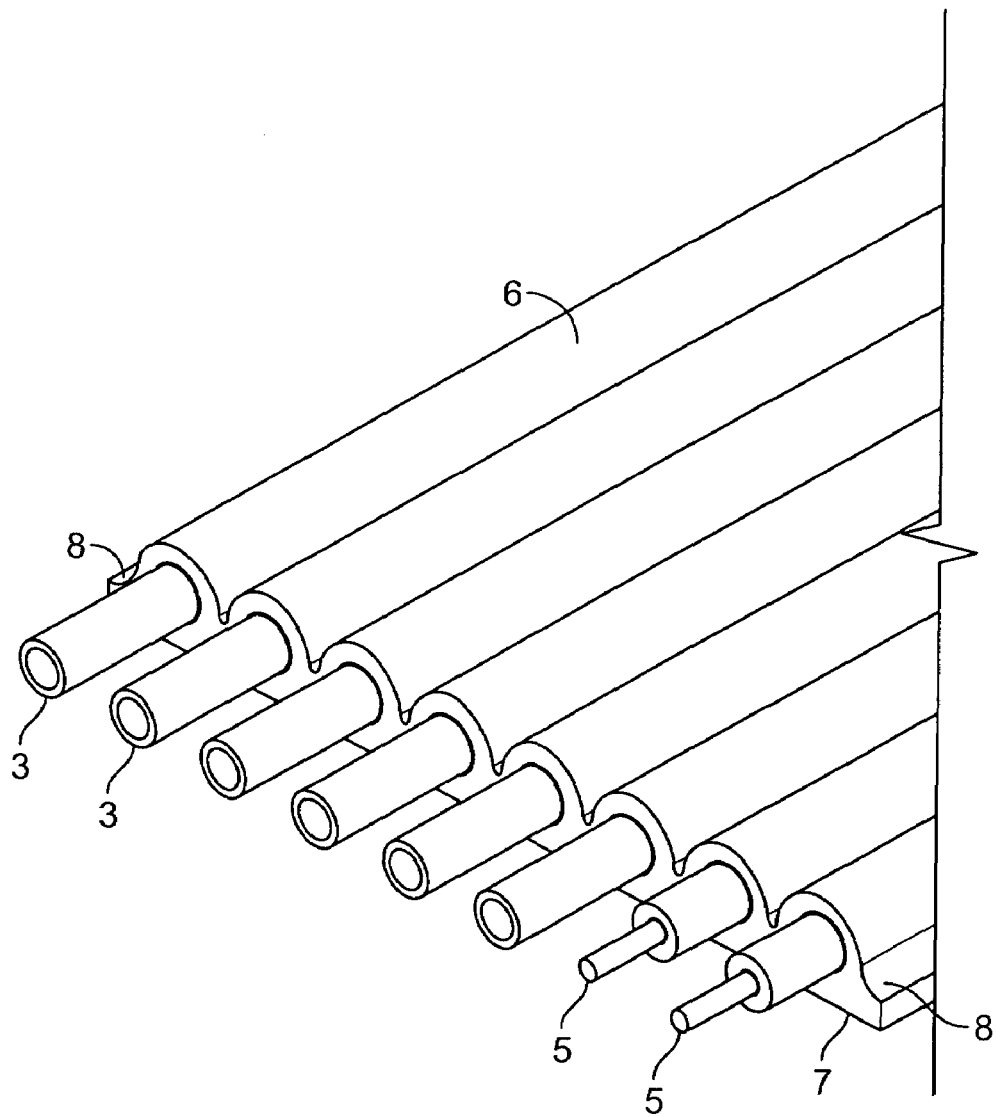
FIG. 4 is a perspective view of a flat strip according to a third embodiment of the invention.

Furthermore, in FIG. 4, a third embodiment of the invention is likewise shown in the form of a flat strip, which regarding its shape substantially corresponds to the second embodiment, but in which the fibers/cables 5 are not arranged in spaces between the conduits 3 but as fiber/cable cords separate form the conduits 3 at one or both longitudinal sides of the flat strip.

In principle, according to the second and third embodiments, the conduits 3 are formed by tubes and possibly the fibers/cables 5 are coated with an insulating layer, wherein the thus formed tubes and fibers/cables are embedded in the envelope forming the flat strip. In both embodiments it is also possible as an alternative, however, comparable to the first embodiment to design the conduits by mandrels which are cast round with the envelope material and are then withdrawn from the hardened envelope material. It also is basically possible, especially also in the second and third embodiment, to form the working conduit 2 by a separate hose or tube-shaped component which is then surrounded by the flat strip spiral.

Figure 5A:
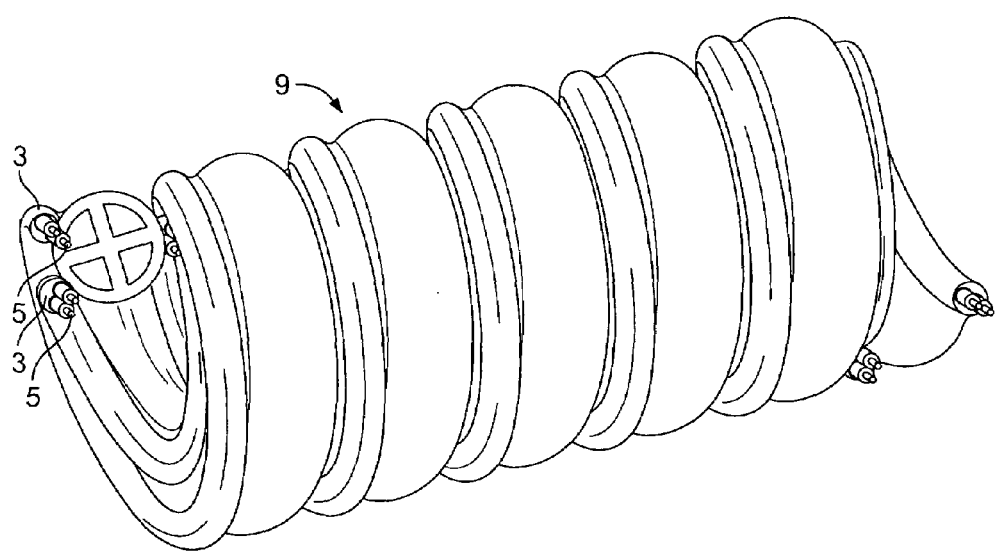
FIGS. 5a, 5b show perspective views of a conduit-fiber-hose package according to a fourth embodiment of the invention.
Figure 5B:
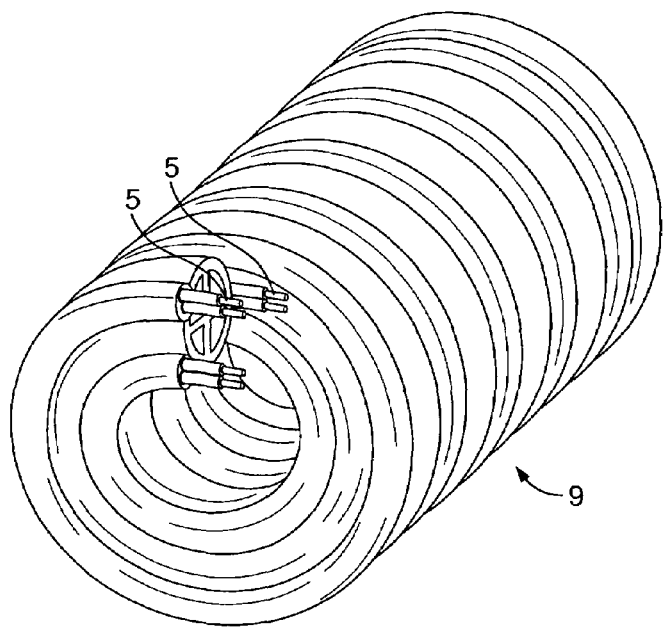

FIGS. 5, 5b show a fourth embodiment for the arrangement of a supply and/or functional conduit.

In accordance with the fourth embodiment of the invention, the supply and/or functional conduits 3 are arranged radially with respect to each other in a kind of hose package 9, wherein the cables or fibers 5 are preferably located at equal angular distances from each other at the outsides of the hose package 9. The hose package 9 consists of an extruded or foamed synthetic rope forming the conduits 3 themselves which in the present case are shaped into quarter circles in their cross-section.

At this point, it shall be pointed out that also a number of supply and/or functional conduits different from four conduits according to the fourth embodiment may be provided. Also, the hose package is guided spirally around the working conduit, as is shown in the first to third embodiments.

Figures 6A, 6B:
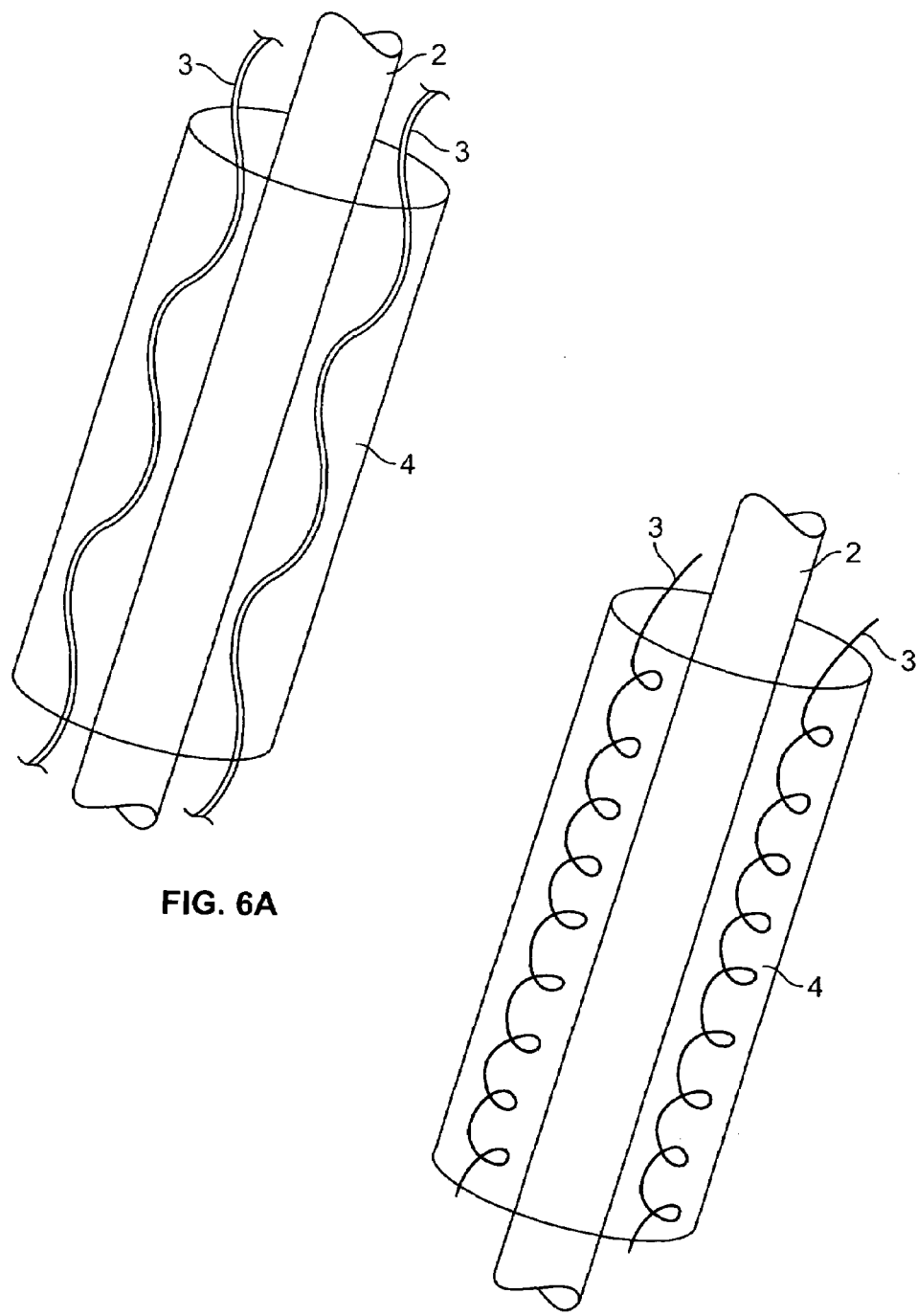
FIGS. 6a, 6b show schematic diagrams of an endoscope shaft according to a fifth preferred embodiment of the invention.

Finally, reference shall be made to a fifth embodiment of the invention according to FIGS. 6a, 6b in which a conduit arrangement alternative to the spiral shape is shown.

Basically, it is crucial to arrange the supply and/or functional conduits 3 in such way that they can be extended in the longitudinal direction of the endoscope shaft 1 by unfolding. The spiral shape is especially suited for this, wherein instead of the spiral around the working conduit 2 each of the supply and/or functional conduits 3 could be disposed per se in spiral shape along the working conduit 1, i.e. radially offset with respect to the same. Furthermore the spiral shape itself may be replaced by a serpentine or zigzag arrangement of the supply and/or functional conduits 3 along the working conduit 1, as is shown by the sketches in FIGS. 6a, 6b.

The invention relates to an endoscope shaft comprising a working conduit 2 and a number of supply and/or functional conduits 3. According to the invention, the supply and/or functional conduits 3 are arranged in spiral, serpentine and/or zigzag shape around or along the working conduit 2, whereby a flexibility and bendability of the endoscope shaft is achieved.

What is claimed is:

1. An endoscope shaft comprising a flexible working conduit and a plurality of supply and/or functional conduits each of which has a portion adjacent to the flexible working conduit, wherein the respective portions of the supply and/or functional conduits are arranged at a predetermined radial distance from the flexible working conduit over the entire axial length thereof, wherein the respective portions of the supply and/or functional conduits adjacent the flexible working conduit are of greater length than the flexible working conduit, wherein the respective portions of the supply and/or functional conduits adjacent to the flexible working conduit are combined into a flat strip which is wound into a spiral shape, and wherein the flat strip has a closed, preferably smooth surface forming the inner wall of the flexible working conduit by the spiral winding of the flat strip.

2. An endoscope shaft according to claim 1, wherein the respective portions of the supply and/or functional conduits adjacent to the flexible working conduit extend spirally around the flexible working conduit.

3. An endoscope shaft according to claim 1, wherein at least an electric line, a glass fiber line and/or a bundle of lines is/are arranged substantially parallel to the respective portions of the supply and/or functional conduits adjacent to the flexible working conduit.

4. An endoscope shaft according to claim 3, wherein the electric line and/or the glass fiber line is/are arranged between the respective portions of the supply and/or functional conduits adjacent to the flexible working conduit.

5. An endoscope shaft according to claim 1, wherein the respective portions of the supply and/or functional conduits adjacent to the flexible working conduit have a rectangular or triangular shape in cross-section.

6. An endoscope shaft comprising a flexible working conduit and a plurality of supply and/or functional conduits each of which has a portion adjacent to the flexible working conduit, wherein the respective portions of the supply and/or functional conduits are arranged at a predetermined radial distance from the flexible working conduit over the entire axial length thereof, wherein the respective portions of the supply and/or functional conduits adjacent the flexible working conduit are of greater length than the flexible working conduit, wherein the respective portions of the supply and/or functional conduits adjacent to the flexible working conduit are combined into a flat strip which is wound into a spiral shape, and wherein individual windings are glued or welded together at their outer sides, thereby sealing the flexible working conduit.

7. An endoscope shaft according to claim 1, wherein the respective portions of the supply and/or functional conduits adjacent to the flexible working conduit have a rectangular or triangular shape in cross-section.

8. An endoscope shaft comprising a flexible working conduit and a plurality of supply and/or functional conduits each of which has a portion adjacent to the flexible working conduit, wherein the respective portions of the supply and/or functional conduits are arranged at a predetermined radial distance from the flexible working conduit over the entire axial length thereof, wherein the respective portions of the supply and/or functional conduits adjacent the flexible working conduit are of greater length than the flexible working conduit, wherein the respective portions of the supply and/or functional conduits adjacent to the flexible working conduit are combined into a flat strip which is wound into a spiral shape, and wherein the respective portions of the supply and/or functional conduits adjacent to the flexible working conduit have a rectangular or triangular shape in cross-section.

9. An endoscope shaft comprising a flexible working conduit and a plurality of supply and/or finctional conduits each of which has a portion adjacent to the flexible working conduit, wherein the respective portions of the supply and/or functional conduits are arranged at a predetermined radial distance from the flexible working conduit over the entire axial length thereof, wherein the respective portions of the supply and/or functional conduits adjacent the flexible working conduit are of greater length than the flexible working conduit, wherein the respective portions of the supply and/or functional conduits adjacent to the flexible working conduit are combined into a flat strip which is wound into a spiral shape, wherein the respective portions of the supply and/or functional conduits adjacent to the flexible working conduit extend spirally around the flexible working conduit, and wherein the respective portions of the supply and/or functional conduits adjacent to the flexible working conduit have a rectangular or triangular shape in cross-section.

* * * * *